(12) United States Patent
Blunn et al.

(10) Patent No.: US 7,014,661 B2
(45) Date of Patent: Mar. 21, 2006

(54) TRANSCUTANEOUS PROSTHESIS

(75) Inventors: Gordon Blunn, North Hertfordshire (GB); Justin Cobb, London (GB); Allen Goodship, Hertfordshire (GB); Paul Unwin, Hertfordshire (GB)

(73) Assignee: University College London, London (GB)

( * ) Notice: Subject to any disclaimer, the term of this patent is extended or adjusted under 35 U.S.C. 154(b) by 0 days.

(21) Appl. No.: 10/311,589

(22) PCT Filed: Jun. 22, 2001

(86) PCT No.: PCT/GB01/02771

§ 371 (c)(1),
(2), (4) Date: Apr. 28, 2003

(87) PCT Pub. No.: WO01/97718

PCT Pub. Date: Dec. 27, 2001

(65) Prior Publication Data

US 2003/0171825 A1 Sep. 11, 2003

(30) Foreign Application Priority Data

Jun. 23, 2000 (GB) .................................. 0015479

(51) Int. Cl.
*A61F 2/28* (2006.01)
(52) U.S. Cl. ............... 623/23.57; 623/11.11; 623/16.11; 623/23.48; 623/23.5; 623/23.76; 623/32; 623/53; 623/57
(58) Field of Classification Search ............ 623/11.11, 623/16.11, 23.48, 23.49, 23.5, 23.55, 23.56, 623/23.57, 23.76
See application file for complete search history.

(56) References Cited

U.S. PATENT DOCUMENTS

| | | | |
|---|---|---|---|
| 3,947,897 A | | 4/1976 | Owens |
| 4,143,426 A | | 3/1979 | Hall et al. |
| 4,158,895 A | | 6/1979 | Frosch et al. |
| 4,330,891 A | | 5/1982 | Brånemark et al. |
| 5,026,397 A | | 6/1991 | Aoki et al. |
| 5,169,597 A | * | 12/1992 | Davidson et al. ........... 428/613 |
| 5,336,268 A | | 8/1994 | Rispeter |
| 5,501,706 A | * | 3/1996 | Arenberg ................. 623/23.56 |
| 5,578,086 A | | 11/1996 | Prescott |
| 5,709,683 A | * | 1/1998 | Bagby ......................... 606/61 |
| 5,723,038 A | * | 3/1998 | Scharnweber et al. ...... 205/107 |
| 5,725,573 A | | 3/1998 | Dearnaley et al. |
| 5,981,827 A | | 11/1999 | Devlin et al. |
| 6,541,024 B1 | * | 4/2003 | Kadiyala et al. ............ 424/426 |

FOREIGN PATENT DOCUMENTS

| | | |
|---|---|---|
| AU | 199657577 B2 | 1/1998 |
| DE | 3439993 A1 | 5/1986 |
| DE | 94 00 720.9 | 6/1995 |
| DE | 198 26 638 A1 | 12/1999 |
| EP | 0 545 542 A1 | 6/1993 |
| EP | 0 547 354 A1 | 6/1993 |
| EP | 0 806 212 A1 | 5/1997 |

(Continued)

*Primary Examiner*—Corrine McDermott
*Assistant Examiner*—William Matthews
(74) *Attorney, Agent, or Firm*—Buchanan Ingersoll PC

(57) ABSTRACT

A transcutaneous prosthesis is disclosed comprising a first component (1) shaped for implantation into a bone (2), a second component (4) intended for location between the bone (2) and the skin, and a third component (5) intended for location exterior to the skin surface, having a low surface energy which deters bacterial adhesion. The second component (4) may carry an adhesion-promoting protein.

5 Claims, 3 Drawing Sheets

| | FOREIGN PATENT DOCUMENTS | | | WO | 97/46179 | 12/1997 |
|----|----|----|----|----|----|----|
| GB | 2 139 095 A | 11/1984 | | | | |
| WO | 89/04153 A1 | 5/1989 | | * cited by examiner | | |

TRANSCUTANEOUS PROSTHESIS

This invention relates to transcutaneous prosthesis and includes a method of fitting a prosthesis having a transcutaneous component to a patient.

Amputation of limbs or digits can occur due to trauma or because of surgical removal. Examples of trauma include loss of fingers in machinery accidents, loss of limbs in car accidents or as a result of land mine explosions. Surgical removal can also be indicated as a result of cardio-vascular disease, diabetes and cancerous tumours to the bone or soft tissues.

After amputation, it is common to fit an external endo-prosthetic device that is attached to the body via by a skin interface. This commonly involves the manufacture of a custom-made socket which is secured to the stump using straps or clamps. A number of disadvantages arise from the use of such endo-prosthetic devices. For example:

(1) Skin is not a satisfactory high load bearing structure and often breaks down under load, becoming inflamed and uncomfortable and, in severe cases, pressure sores are formed which are difficult to heal.

(2) Changes in the shape of the stump may mean that a new custom-made socket is required.

(3) The use of sockets for receiving the stump are commonly sweaty and uncomfortable.

(4) Where a joint is involved, the external prosthesis is usually moved by muscle groups situated at a distance from the attached prosthesis and therefore motion is inefficient and unnatural.

A major object of the present invention is to provide a prosthesis which overcomes some or all of the above disadvantages.

According to one aspect of the present invention there is provided a transcutaneous prosthesis which comprises a first component shaped for implantation into a bone, a second component intended for location between the bone and the skin, the second component having a surface treatment for stimulation of fibroblastic cell proliferation and attachment of epithelial cells and a third component intended for location exterior to the skin surface having a low surface energy which deters bacterial adhesion.

The prosthesis provided by the present invention is thus an intra-osseous transcutaneous prosthesis (ITAP) and has a number of advantages. For example, the first component is attached directly to load-bearing parts of the bony skeleton such that load is transmitted through bone. This means that the patient is able to apply much more power to the prosthesis. Also, motion and perception of movement is more natural because of the bone attachment. Moreover, because the skin takes no part in transmitting the load from the bone to the external part of the prosthesis, there is no pressure on the skin surface which would cause inflammation or discomfort.

The first component is formed with some suitable means for preventing rotation of the component in the bone which may comprise flutes or grooves or functionally similar shaped surfaces. These surfaces may be shaped to fit the profile of the intramedullary cavity, where present. Also, the first component is preferably provided with a surface treatment which encourages osseous integration. Suitable surface treatments include hydroxyapatite which is a hydrated calcium phosphate. The surface may also be formed with small apertures or pits to encourage integration between the bone and the first component. Where micro pits are formed in the surface, these may be of the order of 20 to 500 microns in size, preferably 20 to 100 microns.

The second component extends between the bone and the epithelial surface. This component is provided with a surface treatment for stimulating fibrous tissue ingrowth. Again, this component may be treated with an hydroxyapatite or aluminium oxide coating and the coating treated with materials which encourage the adhesion of epithelial cells to the second component. This component may also have a coating which is porous to encourage soft tissue ingrowth Materials which encourage such growth include adhesion promoting proteins such as fibronectin or laminin. In order to aid adhesion of the fibrous tissue to the second component, the hypodermis is preferably surgically removed during the procedure of installing the prosthesis. The goal is to attach the skin to the implant to prevent movement of the skin and shear forces separating epithelial cells at the interface and underlying dermis and thereby permitting infection to enter between the skin and the prosthesis.

The third component comprises the exterior part of the prosthesis and this has a low surface energy which deters bacterial adhesion. A low surface energy can be achieved by coating this part of the prosthesis with a non-stick material such as a diamond-like carbon, a fluorinated polymer or a silicone polymer.

The prosthesis may be made up from separate components connected together, or two or more of the components may be formed integrally and given appropriate surface treatments.

The external component will preferably include a safety device comprising a linkage which breaks under an unusual load such as, for example, one caused by the patient falling. This will allow the external component to detach from the skeletal and transcutaneous component without causing damage to the bone or to the skin. An additional feature which will protect the fixation of an intramedullary post is an external device which limits torque transmitted to the adjustable fixation. The torque transmitted may be adjustable so that with time, the transmitted torque can be increased, as the internal component integrates with the bone.

In a further preferred embodiment of the present invention the second component may be provided so as to extend outwardly from the first and third components in a manner that increases the external surface area of the second component. The second component may also be provided with through holes which further increase the external surface area and allow growth of tissue through the second component. This has been found to advantageously facilitate the integration of the component with fibrous tissue growth.

The invention is illustrated by the accompanying drawings in which.

Figure 1:
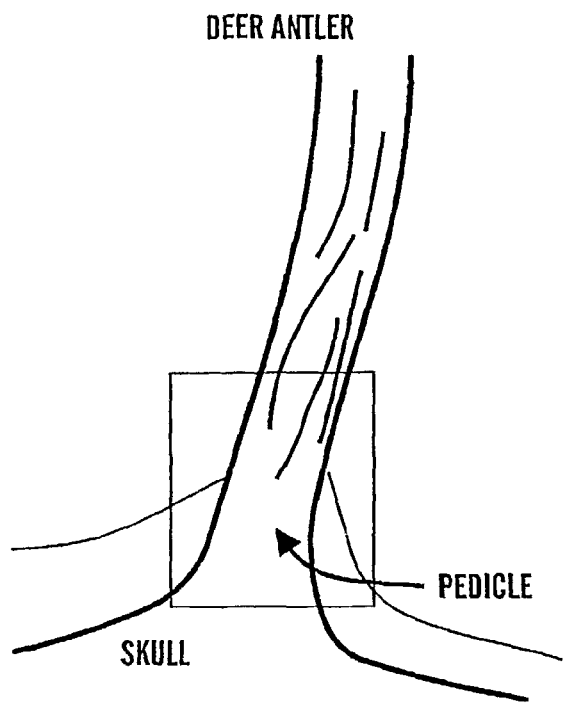
FIGS. 1 and 2 are diagrammatic views through part of a deer's antler and skull.
Figure 2:
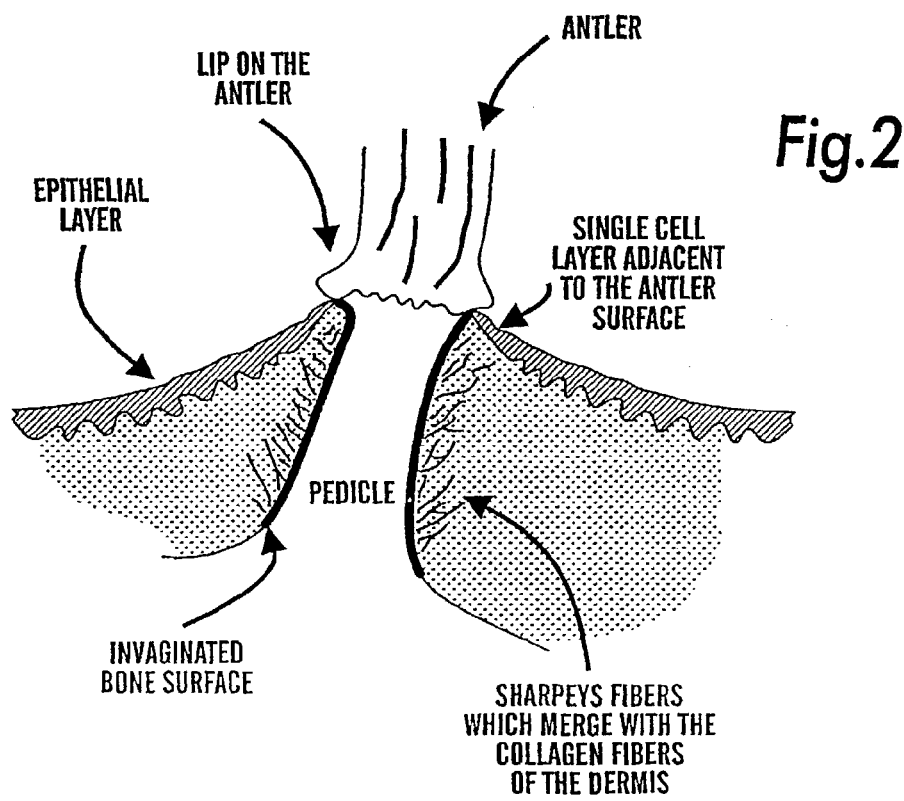

Referring to the drawings, the present invention was in part stimulated by study of the skin-bone interface around red deer antlers. This is a unique structure and may be thought of as a biological model for a transcutaneous implant. The deer antler at periods of the year is very heavily loaded during the rut. Histological examination indicates that the layer of skin epithelial cells become thinner as the epithelial layer approaches the antler, such that at the antler-skin interface an epithelial skin layer is only about one cell thick The dermis is intimately attached to the bone (pedicle) interface. The attachment is achieved through a series of "Sharpeys fibres" which attach to the dermis and to the bone and prevent differential skin movement. Antlers do not normally become infected and the bone structure is invaginated with small pores measuring 18 to 40 microns in diameter. This helps the interface between the dermis and the bone to resist shear stresses. These features are shown in FIGS. 1 and 2 of the accompanying drawings.

Figure 3:
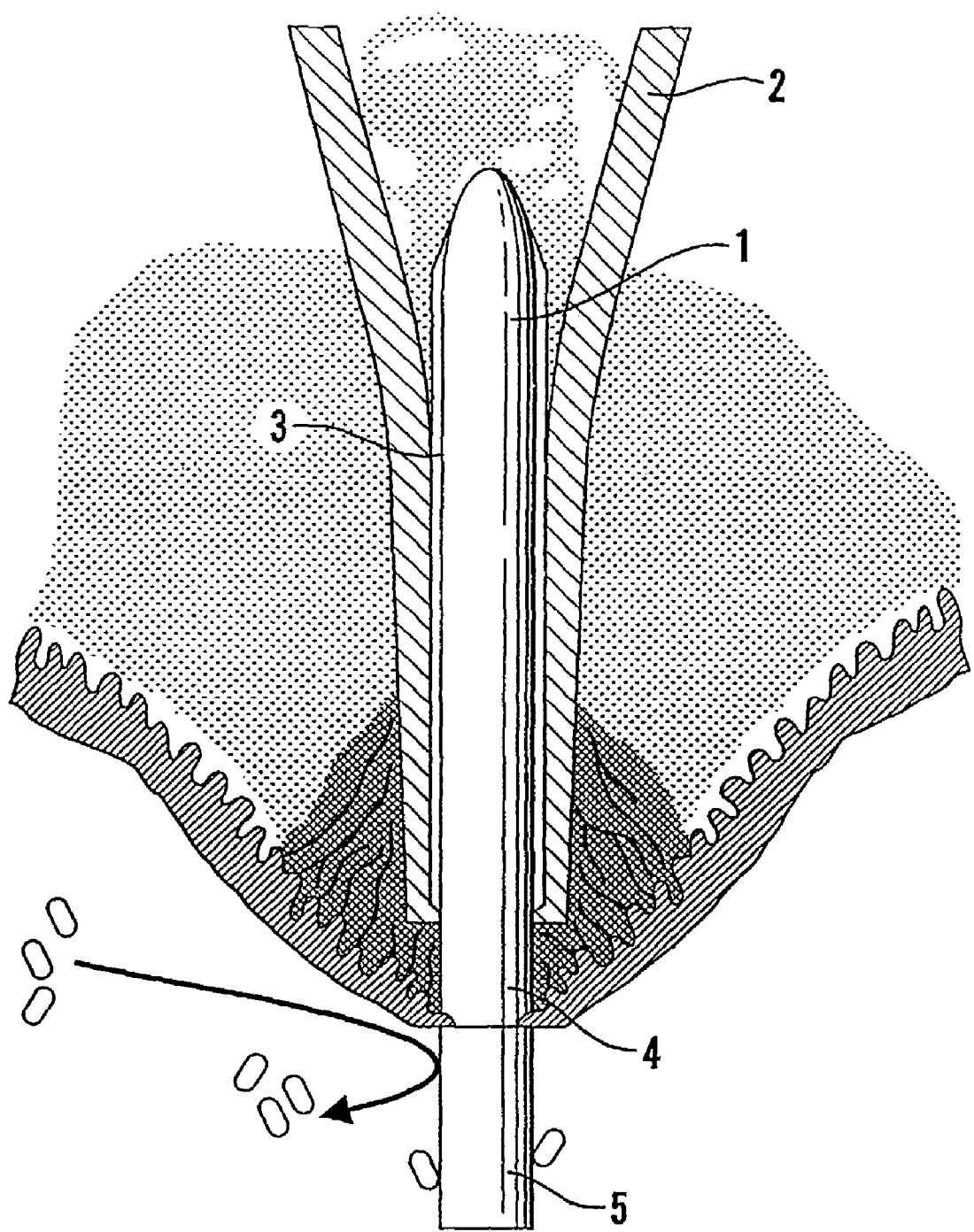
FIG. 3 is a diagrammatic part section showing a transcutaneous prosthesis in accordance with the invention, fitted to a patient.

The prosthesis of the present invention is shown in FIG. 3 and may be considered an artificial analogue of the deer's antler. The prosthesis comprises a first component (1) which is inserted into the intramedullary canal of a bone (2). Component (1) is formed with longitudinally extending cutting flutes which engage in the bone as the prosthesis is inserted into the intramedullary canal and resists rotation The surface of the component (1) may be coated with a material to encourage osseous integration such as a hydroxy apatite material and/or be micro-pitted. The second component (4) extends from the end of the bone to the surface of the skin. This component may be cylindrical as drawn, or could be flattened to a mushroom shape, thereby increasing the surface area over which the soft tissue can be attached. Component (4) is given a surface treatment to encourage attachment of the epithelial to the implant. Such surface treatments include giving the surface a micro-pitted structure and/or coating the surface with adhesion proteins such as laminin or fibronectin which encourage fibrous growth into the surface of the component (4) of the prosthesis.

Prior to installing the prosthesis, the hypodermis is preferably surgically removed. Further, a surface is provided on the second component which is porous and promotes fibrous tissue ingrowth. Suitable materials for coating the surface include alumina oxide ceramics and hydroxy apatite. This surface, preferably after being given a porous surface treatment, is coated with an adhesion promoting protein, e.g. by spraying the prosthesis with a solution of the adhesion-promoting protein, by dipping the prosthesis in a concentrated solution of the protein and freeze drying, or by dipping into a sterile solution of the adhesion-promoting protein prior to implantation The removal of the hypodermis surgically during the amputation and installation procedure assists in stimulating attachment of the skin to the implant and thereby prevents shear forces on the skin separating the epithelial cells at the interface.

The third component (5) of the prosthesis extends from the skin and is given a non-stick surface on its exterior portion Suitable materials include fluorinated polymers such as polytetrafluoroethylene, siliconised polymers and diamond like carbon. The presence of a non-stick surface discourages bacteria from attaching to the prosthesis and helps to prevent infection. The non-stick surface may be applied to the exterior portion of the third component (5) using the technique of chemical vapour deposition (CVD). The use of CVD is well known in the art for applying a surface of diamond-like carbon. When applying a surface layer of diamond, as disclosed in EP-B-0545 542 the method generally involves providing a mixture of hydrogen or oxygen gas and a suitable gaseous carbon compound such as a hydrocarbon, applying energy to that gas to dissociate the hydrogen into atomic hydrogen or the oxygen into atomic oxygen and the carbon into active carbon ions, atoms or CH radicals and allowing such active species to deposit on the substrate to form diamond. The energy to cause dissociation may be provided in a number of ways common to the art, for example by hot filament or by microwave source. A non-stick surface of fluorinated polymer or silicone polymer may be applied to the third component by polymerising a monomer or prepolymer in contact with the component.

It may be convenient to apply the low energy surface treatment to the third component while masking the remaining components of the prosthesis. Also, the second component of the prosthesis may be treated with the adhesion-promoting protein after applying the low energy surface to the third component, and it may be desirable to mask the third component while applying the adhesion-promoting protein.

The third component may be connected to an artificial limb or digit. For example, in the case of a replacement finger or part finger, the first component may be implanted into the remaining bone with the second component instituting the transcutaneous portion, and the third component extending beyond the severed stump. An artificial digit or part digit can then be attached to the third component.

The prosthesis may be implanted either in a one-stage procedure or in a two-stage procedure where the first component is implanted into the bone and allowed to integrate before the transcutaneous part is attached.

Figure 4:
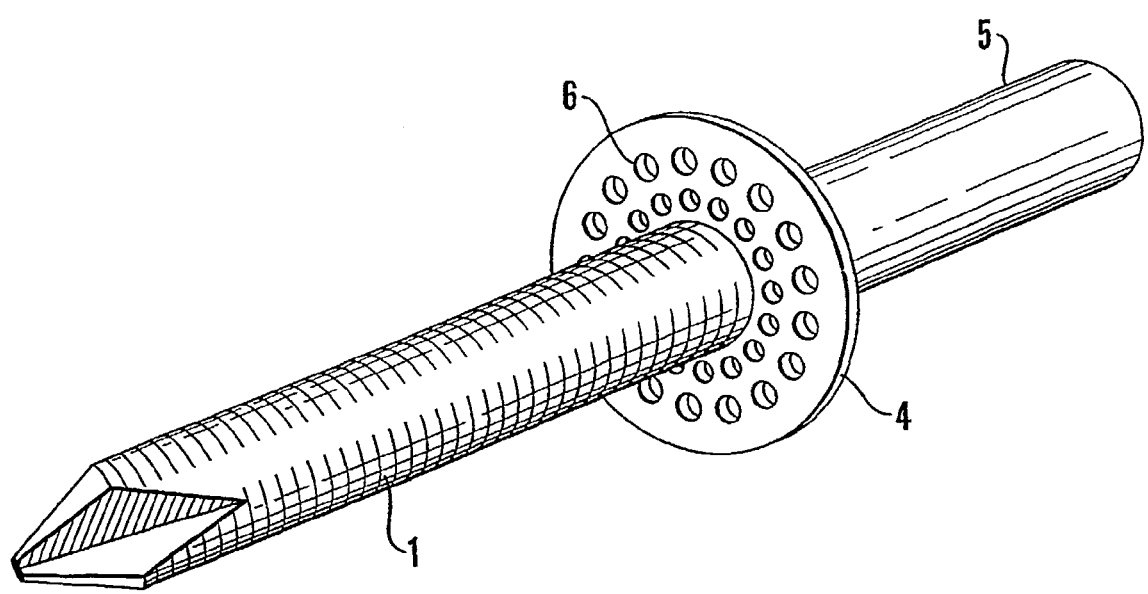
FIG. 4 is a perspective view of a preferred embodiment of a prosthesis in accordance with the present invention drawn on a larger scale compared with FIG. 3.

There is shown in FIG. 4 a further preferred embodiment of the present invention wherein the second component (4) is extended in an outward direction perpendicular to the first and third components in a plate like form. This feature provides the second component (4) with a large surface area which advantageously facilitates the integration of the second component (4) with fibrous tissue growth. As also shown in FIG. 4, through holes (6) may be provided in the plate like extension of the second component (4), which further increase the external surface area and also allowing tissue to grow through the second component further facilitating integration. Although the above description refers to a series of components, it will be appreciated that each component may be a portion of an integral element manufactured from a single piece of material. It is, however, preferred that a frangible linkage is provided between the third and second components or between the second and first component, so that in the event that a high load is applied to the third component, or to a member attached thereto, the linkage will fair so as to protect the implanted bone from injury.

While the present invention has been described with particular reference to the provision of a prosthesis for replacement of lost digits or limbs, the invention is also applicable to other prosthesis which extend through the skin, e.g. dental implants.

What is claimed is:

1. A method of installing a transcutaneous prosthesis which comprises a first component shaped for implantation into a bone, a second component adapted for location between the bone and the skin, the second component having a surface treatment for stimulation of fibroblastic cell proliferation and attachment of epithelial cells and a third component adapted for location to extend from the skin surface and the third component having an outer surface, wherein the outer surface of the third component has a surface energy that is lower than a surface energy of the first and second components and which is low enough to deter bacterial adhesion, the method comprising:

implanting the first component into a bone such that a transition from the second component to the third component is essentially at the surface of the skin and the third component extends from the skin surface when the first component is implanted in a bone.

2. The method of claim 1, wherein the implanting step includes inserting the first component into an intramedullary canal of the bone.

3. The method of claim 2, wherein the second component extends from an end of the bone to the surface of the skin when the first component is implanted in the bone.

4. The method of claim 1, wherein prior to installing the prosthesis the skin is reduced in thickness.

5. The method of claim 4, wherein the skin hypodermis is surgically removed.

* * * * *